United States Patent [19]

Krause et al.

[11] Patent Number: 5,780,389
[45] Date of Patent: Jul. 14, 1998

[54] MICROENCAPSULATED PLANT PROTECTION AGENTS COMPRISING DIBENZYLTOLUENES AS SOLVENT, A PROCESS FOR THEIR PREPARATION, AND THEIR USE

[75] Inventors: Hans-Peter Krause; Thomas Maier, both of Hofheim; Jean-Paul Schoeni, Wiesbaden; Anna Waltersdorfer, Frankfurt, all of Germany

[73] Assignee: Hoechst Schering AgrEvo GmbH, Berlin, Germany

[21] Appl. No.: 534,234

[22] Filed: Sep. 26, 1995

[30] Foreign Application Priority Data

Sep. 28, 1994 [DE] Germany ............ 44 34 638.7

[51] Int. Cl.$^6$ .............. A01N 25/02; A01N 25/28
[52] U.S. Cl. .............. 504/116; 424/405; 424/490; 514/963; 514/971
[58] Field of Search .............. 504/116; 71/DIG. 1; 424/405, 490; 514/963, 971

[56] References Cited

U.S. PATENT DOCUMENTS

| 4,107,292 | 8/1978 | Nemeth | 424/78 |
| 4,124,526 | 11/1978 | Allart et al. | 252/316 |
| 4,640,709 | 2/1987 | Beestman | 71/100 |
| 4,857,406 | 8/1989 | Schwab et al. | 71/DIG. 1 |
| 5,225,278 | 7/1993 | Keilbania, Jr. et al. | 71/DIG. 1 |
| 5,435,992 | 7/1995 | Ramesch et al. | 210/734 |

FOREIGN PATENT DOCUMENTS

| A-0 158 449 | 10/1985 | European Pat. Off. |
| 0322820 | 7/1989 | European Pat. Off. |
| 0368285 | 5/1990 | European Pat. Off. |
| A-0 379 379 | 7/1990 | European Pat. Off. |
| 2689729 | 10/1993 | France . |
| 2185685 | 7/1987 | United Kingdom . |

*Primary Examiner*—S. Mark Clardy
*Attorney, Agent, or Firm*—Frommer Lawrence & Haug LLP

[57] ABSTRACT

The present invention relates to microcapsules containing water-insoluble, liquid active ingredients or mixtures thereof, which are employed principally in the sector of plant protection and in which the solvent which is likewise present within the capsule is a liquid substance comprising two or more aromatic rings.

The microencapsulation of plant protection agents, especially the envelopment of water-insoluble, liquid or solid active particles in water-based mixed-phase systems, has developed in recent years to become a standard formulation technique.

7 Claims, No Drawings

MICROENCAPSULATED PLANT PROTECTION AGENTS COMPRISING DIBENZYLTOLUENES AS SOLVENT, A PROCESS FOR THEIR PREPARATION, AND THEIR USE

The present invention relates to microcapsules containing water-insoluble, liquid active ingredients or mixtures thereof, which are employed principally in the sector of plant protection and in which the solvent which is likewise present within the capsule is a liquid substance comprising two or more aromatic rings.

The microencapsulation of plant protection agents, especially the envelopment of water-insoluble, liquid or solid active particles in water-based mixed-phase systems, has developed in recent years to become a standard formulation technique.

Microcapsule dispersions are stored and used like other liquid formulations. However, in relation to emulsifiable concentrates, for example, their retarded release of active ingredient often gives them advantages such as, for example, reduced toxicity to mammals, more favorable leaching behavior, reduced evaporation rates and the like. The results of this for the user are that the number of applications required can be limited and the overall quantity of active ingredient to be applied can be reduced.

In general, the said technique of enveloping active particles in a water-based mixed-phase system is carried out by a procedure in which, prior to the formation of the microcapsules, the water-insoluble, noncontinuous phase comprises a polar, liquid or low-melting active ingredient and, if desired, a nonwater-soluble agent which is miscible therewith and forms the capsule wall. Examples of this can be found, for instance, in U.S. Pat. No. 4,640,709 and U.S. Pat. No. 4,107,292. The agent which forms the capsule wall may alternatively be soluble in water and may accordingly be present in the continuous dispersion phase. This possibility is described, for example, in EP-A-0,026,914.

However, there are cases in which the active ingredient has an excessively high melting point, and solvent-free operation is not readily possible. In other cases, the active ingredient is indeed liquid but is of such low polarity that it does not mix sufficiently with the agent which forms the capsule wall (and which generally contains polar groups), or that troublesome flocculation occurs.

In such cases, it is advisable to use a polar solvent whose solubility in water is nevertheless so low that, in the interim emulsion at the beginning of the encapsulation process, neither crystallization of active ingredient nor flocculation occur to disrupt the process.

For this purpose, a variety of aromatic solvents have already been employed. Examples are toluene (GB-A-1,310, 866), xylene (EP-A-270 742, U.S. Pat. No. 3,577,515), xylylphenylethane (EP-A-322 820), dimethyl phthalate (EP-A-399 911), but especially naphtha having a boiling range of about 240°–290° C. (U.S. Pat. No. 4,285,720, EP-A-158 449, EP-A-571 396).

The latter solvent, for example, is prepared by Exxon under the name "Solvesso 200" and is a solvent standard in liquid plant protection compositions.

The object of the invention is to provide a solvent for the microencapsulation of active ingredients or mixtures thereof, which solvent retains the advantages—known from the prior art—of preventing the crystallization of active ingredient or flocculation and which in addition increases the biological activity of the active ingredients or mixtures thereof.

It has now unexpectedly been found that, in a comparison of microcapsule dispersions which contain "Solvesso 200" as solvent with microcapsule dispersions whose solvents come from a group consisting of liquid substances having two or more aromatic rings, a stronger biological action is present in the latter.

The invention therefore provides microcapsules which enclose a water-insoluble, liquid active ingredient or a mixture thereof and which are composed of a solid or liquid active ingredient or mixture thereof for encapsulation and of one or more solvents comprising alkylated biphenyls and dibenzyltoluenes.

The term microcapsules refers to nonreactive carriers which surround active ingredients or mixtures thereof and whose walls consist of polymeric structures which contain, for example, urea, urethane, amide, ester, carbonate or sulfonamide groups. It is known that they can be prepared by boundary-phase microencapsulation via polycondensation.

The biological activity of the microencapsulated plant protection agents according to the invention is defined as the quotient of the quantity of formulated active ingredient (ppm a.i.) applied in the test system (see Examples) to the percentage proportion of pests or fungi.

The abbreviation ppm a.i. denotes parts per million (based on the as-applied formulation of the active ingredient in water) of active ingredient.

A liquid or solid substance is dissolved in one of the solvents according to the invention, and a (first) material which forms the capsule wall and which is insoluble in water but may well be soluble in oil is added.

This organic phase is emulsified with stirring into the aqueous phase of surface-active substances. This dispersion solution contains appropriate auxiliaries and, if desired, a second agent which forms the capsule wall.

The desired droplet size in the interim emulsion which is initially formed on combination of the organic and aqueous phase is from 1 to 100 microns, preferably 5 to 20 microns.

The water and/or the second agent which forms the capsule wall from the aqueous dispersion phase then reacts at the interface with the agent which forms the capsule wall of the organic phase, to form solid envelopes around the emulsion droplets.

As already stated above, the capsule content comprises a liquid or solid active ingredient or a mixture thereof, and one or more liquid substances whose chemical structure comprises two or more aromatic rings.

The substances to be encapsulated are preferably liquids, oils, low-melting substances, or solids which are soluble in organic solvents, whose water-solubility is low and which do not react with the agent which forms the capsule wall.

Such substances are preferably understood to include active plant protection ingredients such as, for example, the insecticides dimethyl(4-ethoxyphenyl)(3-(4-fluoro-3-phenoxy)phenyl)propylsilane (silafluofen), 4-(cis-4-tert-butylcyclohexylamino)-5-chloro-6-ethylpyrimidine, (1,4,5, 6,7,7-hexachloro-8,9,10-trinorborn-5-en-2,3-ylenebismethylene) sulfite (endosulfan), 7-chlorobicyclo-[3.2.0]hepta-2,6-dien-6-yl dimethyl phosphate (heptenophos), O,O-diethyl O-(1-phenyl-1H-1,2,4-triazol-3-yl) thiophosphate (triazophos), (S)-alpha-cyano-3-phenoxybenzyl (1R)-cis-3-(dibromovinyl)-2,2-dimethylcyclopropanecarboxylate (deltamethrin), and O,O-diethyl O-(4-nitrophenyl) thiophosphate (parathion-ethyl) (the active ingredients mentioned may be used in plant protection but also in veterinary medicine against ectoparasites); the herbicides 2,6-dinitro-N,N-dipropyl-4-trifluoromethyl-aniline (trifluralin) and 2-chloro-2',6'- diethyl-N-(methoxymethyl)acetanilide (alachlor); and the fungicide 1-anilino-4,6-dimethylpyrimidine (pyrimethanil).

Similarly, it is also possible to encapsulate mixtures of active ingredients having the same or different indications.

The group of the solvents according to the invention is formed by one or more liquid substances whose chemical structure comprises two or more aromatic rings, and in particular a mixture of isomeric dibenzyltoluenes a mixture of alkyl-substituted biphenyls where the substituents are preferably $C_1$–$C_{20}$-alkyl radicals which are independently from each another straight-chain or branched.

A mixture of isomeric dibenzyltoluenes is produced by Hüls AG in Marl under the name Marlotherm S®. It is employed in industry as a heat-transfer medium.

The use of dibenzyltoluene in the plant protection sector has been described. EP-A-400 923 teaches the use of this liquid as being particularly suitable for insecticidal applications in the household sector, since it does not irritate the mucosae and has only a slight intrinsic odor.

JP 1 009 901 describes the emulsion-stabilizing effect of dibenzyltoluene.

A mixture of alkyl-substituted biphenyls is produced by the company BVA Oils, Wixom, Mich. under the name BVA XK3®. Alkylated biphenyls are known as solvents in printing, for example in microcapsules for copier papers as described, for instance, in DE-A-3 715 649 and JP 74-5781 (Showa). In a case similar to that for dibenzyltoluene, EP-A-567 368 teaches the use in liquid plant protection compositions as a virtually odorless solvent with only slight skin irritation.

The term water-insoluble agents which form the capsule wall, in the organic phase, refers to substances such as, for example, chlorides of polybasic carboxylic acids, and oil-soluble prepolymers containing free isocyanate, chloroformate and chlorosulfonyl groups, etc.

Particularly good results are obtained, for example, using an isocyanate prepolymer mixture which is obtained by reacting 2 to 3 mol of 1,2,6-hexanetriol and/or 1,1,1-trimethylolpropane, 1 mol of 1,3-butanediol and 1 mol of polypropylene glycol 1000 with 8 mol of tolylene di-isocyanate, with a markedly substoichiometric amount of polyols employed. A particularly suitable solvent for the isocyanate prepolymer is a mixture of butyl acetate and xylene in a weight ratio of from 5:1 to 1:5.

The concentration in the organic phase is from 1 to 30% by weight, preferably from 2 to 20% by weight. It is not limited in principle but is limited for purely practical reasons; for instance, the viscosity of the finished microcapsule dispersion often increases so greatly, as the prepolymer concentration in the organic phase rises, that pourability suffers.

As auxiliaries which are used to stabilize the emulsion which is formed initially and the microcapsule dispersion formed therefrom by curing, the aqueous phase preferably contains from 0.5 to 10% by weight of a protective colloid which can preferably be composed, for example, of cellulose derivatives which are soluble or dispersible in water, such as carboxymethylcellulose, hydroxyethylcellulose or carboxymethylethylcellulose, polyvinyl alcohol and/or gum arabic. However, it is also possible to add nonionic, anionic or cationic surface-active substances in quantities of from 0.1 to 10% by weight, for instance block copolymers of ethylene oxide and propylene oxide (capped if desired by aliphatic or aromatic radicals), ligninsulfonates, substitution derivatives of naphthalenesulfonic acid, and the like.

The quantity of the substances mentioned here which is added depends on the nature and composition of the organic phase to be dispersed, on the molecular weight of the active ingredient for encapsulation, on the desired particle size, on the reaction temperature and time, and on the stirring time and stirring speed, and can readily be determined in each individual case by preliminary experiments.

The second, water-soluble agent which forms the capsule wall may be a polyfunctional amine, a polyfunctional phenol, a polyfunctional alcohol (which may if desired also include a portion of the polyvinyl alcohol employed in a stoichiometric excess) and, where the oil-soluble agent which forms the capsule wall comprises free isocyanate groups, may be water itself.

Especially when the batch quantities are relatively large, it is expedient to add an antifoam such as triisobutyl phosphate.

Unwanted deviations of the pH in the reaction mixture can be prevented by addition of sodium hydroxide solution during the curing process.

The invention also provides aqueous microcapsule dispersions which comprise preferably 1–30% by weight, especially 2–20% by weight of the microcapsules according to the invention, and, if desired, 0.5–10% by weight of the abovementioned auxiliaries. After dilution to a consistency which is compatible with their use, they are applied in the form of aqueous dispersions.

The microencapsulated plant protection agents according to the invention in the form of pest-control compositions show good compatibility with plants and favorable toxicity to warm-blooded creatures, and at the same time are suitable for controlling animal pests, especially insects, arachnids, helminths and molluscs, and very preferably for controlling insects and arachnids which are encountered in agriculture, in animal breeding, in forestry, in the protection of stored products and materials and in the hygiene sector. They are active against normally sensitive and resistant species and against all or individual stages of development. The abovementioned pests include:

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Eotetranychus spp., Oligonychus spp., Eutetranychus spp.*

From the order of the Isopoda, for example, *Oniscus asselus, Armadium vulgar, Porcellio scaber.*

From the order of the Diplopoda, for example, *Blaniulus guttulatus.*

From the order of the Chilopoda, for example, *Geophilus carpophagus, Scutigera spp.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea madeirae, Blatella germanica, Acheta domesticus, Gryllotalpa spp., Locusta migratoria migratorioides, Melanoplus differentialis, Schistocerca gregaria.*

From the order of the Isoptera, for example, *Reticulitermes spp.*

From the order of the Anoplura, for example, *Phylloera vastatrix, Pemphigus spp., Pediculus humanus corporis, Haematopinus spp., Linognathus spp.*

From the order of the Mallophaga, for example, *Trichodectes spp., Damalinea spp.*

From the order of the Thysanoptera, for example, *Hercinothrips femoralis, Thrips tabaci.*

From the order of the Heteroptera, for example, *Eurygaster spp., Dysdercus intermedius, Piesma quadrata, Cimex lectularius, Rhodnius prolixus, Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus spp., Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima, Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylloides chrysocephala, Epilachna varivestis, Atomaria spp., Oryzaephilus surinamensis, Anthonumus spp., Sitophilus spp., Otiorrhynchus sulcatus, Cosmopolites sordidus, Ceuthorrynchus assimilis, Hypera postica, Dermestes spp., Trogoderma, Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis, Costelytra zealandica.*

From the order of the Hymenoptera, for example, *Diprion spp., Hoplocampa spp., Lasius spp., Monomorium pharaonis, Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hypobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae, Tipula paludosa.*

From the order of the Siphonaptera, for example, *Xenopsylla cheopsis, Ceratophyllus spp.*

From the order of the Arachnida, for example, *Scorpio maurus, Latrodectus mactans.*

From the class of the helminths, for example, Haemonchus, Trichostrongulus, Ostertagia, Cooperia, Chabertia, Strongyloides, Oesophagostomum, Hyostrongulus, Ancylostoma, Ascaris and Heterakis and Fasciola and phytopathogenic nematodes, for example those of the genera Meloidogyne, Heterodera, Ditylenchus, Aphelenchoides, Radopholus, Globodera, Pratylenchus, Longidorus and Xiphinema.

From the class of the Gastropoda, for example, *Deroceras spp., Arion spp., Lymnaea spp., Galba spp., Succinea spp., Biomphalaria spp., Bulinus spp., Oncomelania spp.*

From the class of the bivalves, for example, *Dreissena spp.*

The plant protection compositions according to the invention which comprise fungicidal active ingredients are distinguished by an outstanding fungicidal action. Fungal pathogens which have already penetrated the plant tissue can be controlled curatively with success. The spectrum of action of such compositions spans a variety of economically important, phytopathogenic fungi, for example *Plasmopara viticola, Erysiphe graminis* and *Puccinia recondita.*

The plant protection compositions according to the invention which comprise herbicides are outstandingly suited to the control of unwanted plant growth. They are applied after dilution with water to the plants, to plant seeds or to the cultivation areas.

The practical implementation of the process for the preparation of the microcapsules is familiar to the person skilled in the art. Further details are given, for example, in DE-A-2 757 017.

The Preparation Examples which follow are intended to illustrate the invention without, however, limiting it.

EXAMPLES

Formulation Examples

Example 1

2 g of a polyvinyl alcohol having a degree of hydrolysis of 83% and a viscosity of 3 mPa.s, 4.2% of glycerol, 1.7 g of a block copolymer of 73% by weight ethylene oxide on a polypropylene oxide of molecular mass 2300, and 0.9 g of ®Reax 88B (a ligninsulfonate from West Waco, USA) are dissolved in 47.2 g of water. To this solution is added with vigorous stirring at room temperature the organic phase consisting of: 20 g of ®Marlotherm S, 20 g of 4-(cis-4-tert-butylcyclohexylamino)-5-chloro-6-ethyl-pyrimidine (an insecticide), 1 g of N-octylpyrrolidone, and 3 g of the 50% strength solution of a prepolymer in a 1:1 mixture of xylene and butyl acetate; the prepolymer is obtained by reacting 8 mol of tolylene diisocyanate (isomer ratio 2,4:2,6—80:20) with 1,2,6-hexanetriol, 1,3-butanediol and polypropylene glycol 1000 in a molar ratio of 3:1:1.

After 5 minutes, the stirring speed is reduced, and stirring is continued at room temperature for 15 hours.

The result is a homogeneous microcapsule dispersion with an average capsule diameter of 6 microns.

Example 2

Formulation is carried out as in Example 1.
Composition:
  20% by weight of insecticidal active ingredient as in Example 1
  20% by weight of ®Marlotherm S
  1% by weight of N-octylpyrrolidone
  3% by weight of prepolymer solution
  3.7% by weight of polyvinyl alcohol
  4.2% by weight of glycerol
  0.9% by weight of ®Reax 88B
  47.2% by weight of water The microcapsules have an average diameter of 14 microns.

Example 3

Formulation is carried out as in Example 1.
Composition:
- 20% by weight of insecticidal active ingredient as in Example 1
- 19% by weight of ®Marlotherm S
- 1% by weight of N-octylpyrrolidone
- 3% by weight of prepolymer solution
- 2.08% by weight of polyvinyl alcohol
- 0.1% by weight of ®Rhodopol 23 (thickener)
- 4% by weight of glycerol
- 5.58% by weight of block copolymer
- 39.2% by weight of water The microcapsules have an average diameter of 7 microns.

Example 4 (Comparison Example 1)

Formulation is carried out as in Example 1.
Composition:
- 20% by weight of insecticidal active ingredient as in Example 1
- 20% by weight of ®Solvesso 200
- 3% by weight of prepolymer solution
- 1.65% by weight of polyvinyl alcohol
- 4.2% by weight of glycerol
- 2.06% by weight of block copolymer
- 0.9% by weight of ®Reax 88B
- 48.19% by weight of water The microcapsules have an average diameter of 14 microns.

Example 5 (Comparison Example 1)

Formulation is carried out as in Formulation Example 1.
Composition:
- 20% by weight of insecticidal active ingredient as in Example 1
- 19% by weight of ®Solvesso 200
- 3% by weight of prepolymer solution
- 2.1% by weight of polyvinyl alcohol
- 1.9% by weight of block copolymer
- 0.1% by weight of ®Rhodopol 23 (thickener)
- 4% by weight of glycerol
- 49.9% by weight of water The microcapsules have an average diameter of 9 microns.

Example 6

Formulation is carried out as in Formulation Example 1.
Composition:
- 28% by weight of endosulfan
- 23% by weight of ®marlotherm S
- 2% by weight of N-octylpyrrolidone
- 3% by weight of prepolymer solution
- 2.1% by weight of polyvinyl alcohol
- 9.1% by weight of block copolymer
- 0.1% by weight of ®Rhodopol 23
- 3.5% by weight of glycerol
- 29.2% by weight of water The microcapsules have an average diameter of 8 microns.

Example 7 (Comparison Example)

Formulation is carried out as in Formulation Example 1.
Composition:
- 28% by weight of endosulfan
- 23% by weight of ®Solvesso 200
- 3% by weight of prepolymer solution
- 2.1% by weight of polyvinyl alcohol
- 1.8% by weight of block copolymer
- 0.1% by weight of ®Rhodopol 23
- 3.5% by weight of glycerol
- 38.5% by weight of water The microcapsules have an average diameter of 11 microns.

Example 8

Formulation is carried out as in Formulation Example 1.
Composition:
- 18% by weight of fluoroglycofen-ethyl (a herbicide)
- 19% by weight of ®Marlotherm S
- 1% by weight of N-octylpyrrolidone
- 3% by weight of prepolymer solution
- 4.7% by weight of polyvinyl alcohol
- 2.1% by weight of block copolymer
- 3% by weight of glycerol
- 49.2% by weight of water The microcapsules have an average diameter of 13 microns.

Example 9

Formulation is carried out as in Formulation Example 1.
Composition:
- 15% by weight of triadimefon (a fungicide)
- 17% by weight of ®Marlotherm S
- 1% by weight of N-octylpyrrolidone
- 3% by weight of prepolymer solution
- 1.8% by weight of polyvinyl alcohol
- 3.5% by weight of block copolymer
- 3% by weight of glycerol
- 54.7% by weight of water The microcapsules have an average diameter of 9 microns.

Biological Examples

Example 10

Test organism: *Plutella xylostella*

Host plant: *Brassica oleracea cv. capitata*

Application method: Dipping of the host plant prior to infestation with test organisms Period of test: 4 days

| Formulation | ppm a.i./% mortality | |
|---|---|---|
| | 16 | 8 |
| Example 1 | 95 | 80 |
| Example 2 | 60 | 30 |
| Example 3 | 70 | 50 |

Example 11

Test organism: *Tetranychus urticae*

Host plant: *Phaseolus vulgaris*

Application method: Spraying until beginning of runoff

Period of test: 7 days

| Formulation | ppm a.i./% mortality | |
|---|---|---|
| | 8 | 4 |
| Example 1 | 100 | 40 |
| Example 2 | 95 | 70 |
| Example 3 | 70 | 80 |
| Example 5 | 50 | 30 |

Example 12

Test organism: *Aphis fabae*

Host plant: *Vicia faba*

Application method: Spraying until beginning of runoff

Period of test: 3 days

| Formulation | ppm a.i./% mortality | |
|---|---|---|
| | 1 | 0.5 |
| Example 1 | 90 | 80 |
| Example 2 | 80 | 60 |
| Example 3 | 80 | 60 |
| Example 5 | 60 | 40 |

-continued

| Formulation | ppm a.i./% mortality | |
|---|---|---|
| | 16 | 8 |
| Example 4 (= Comparison Example 1) | 15 | 10 |

Example 13

Test organism: *Musca domestica*

Application method: Coating of the inner surface of a glass Petri dish with an aqueous dilution of the formulation. After drying, infestation with test organisms Period of test: 3 hours

| Formulation | ppm a.i./% mortality 12 days after application 63 |
|---|---|
| Example 6 | 90 |
| Example 7 | 20 |

We claim:

1. A microcapsule containing a water-insoluble component, which component comprises a solid or liquid active plant protection ingredient or a mixture thereof and a mixture of isomeric dibenzyltoluenes as solvent.

2. A microcapsule as claimed in claim 1, wherein the alkyl substituents have 1–20 carbon atoms and are independently from each another straight-chain or branched.

3. A microcapsule as claimed in claim 1, wherein the active ingredient is from the group consisting of insecticides, herbicides and fungicides.

4. An aqueous microcapsule dispersion comprising a microcapsule as claimed in claim 1.

5. A process for the preparation of a microcapsule as claimed in claim 1, which comprises dissolving a liquid or solid active ingredient or a mixture thereof in a solvent and adding a first material which forms the capsule wall and which is soluble in water but not in oil, and emulsifying the organic phase with an aqueous dispersant solution which contains if desired a second material which forms the capsule wall.

6. A method of controlling harmful fungi, which comprises applying an effective amount of a dispersion as claimed in claim 4 to these harmful fungi or to the plants, areas or substrates infected by them.

7. A method of controlling pests, which comprises applying an effective amount of a dispersion as claimed in clim 4 to these pests or to the plants, areas or substrates infected by them.

* * * * *